United States Patent [19]  [11] 3,987,302
Hurst et al.  [45] Oct. 19, 1976

[54] RESONANCE IONIZATION FOR ANALYTICAL SPECTROSCOPY

[75] Inventors: George S. Hurst, Oak Ridge; Marvin G. Payne, Harriman; Edward B. Wagner, Burchfield Heights, all of Tenn.

[73] Assignee: The United States of America as represented by the United States Energy Research and Development Administration, Washington, D.C.

[22] Filed: Aug. 27, 1975

[21] Appl. No.: 608,377

[52] U.S. Cl. .................................. 250/283; 250/282
[51] Int. Cl.² ........................................ B01D 59/44
[58] Field of Search ............ 250/281, 282, 283, 284

[56] References Cited
UNITED STATES PATENTS 2,950,389  8/1960  Paul et al. ........................... 250/284
3,772,519  11/1973  Levy et al. ........................... 250/284

Primary Examiner—Davis L. Willis
Attorney, Agent, or Firm—John A. Horan; David S. Zachry; Louis M. Deckelmann

[57] ABSTRACT

This invention relates to a method for the sensitive and selective analysis of an atomic or molecular component of a gas. According to this method, the desired neutral component is ionized by one or more resonance photon absorptions, and the resultant ions are measured in a sensitive counter. Numerous energy pathways are described for accomplishing the ionization including the use of one or two tunable pulsed dye lasers.

10 Claims, 6 Drawing Figures

0 ——————————————————— GROUND STATE

RESONANCE IONIZATION FOR ANALYTICAL SPECTROSCOPY

This invention was made in the course of, or under, a contract with the Energy Research and Development Administration.

BACKGROUND OF THE INVENTION

This invention relates generally to the field of analytical spectroscopy and more particularly to methods for the analysis of gases utilizing the generation of ions by photon absorption, involving at least one resonance step, and the measurement of the ionization charge. Where saturation is achieved, the number of ions pairs is numerically equivalent to the number of analyzed species.

One general method known in the art for the determination of a component of a gas is to bring about excited states of an atom of the component by any of several processes and to study the light emitted by these excited states as they return to the ground state. This has numerous problems due to the nature of the states and the light emitted. With most methods of excitation, for example, a number of excited states will be produced at characteristic energy levels and each giving rise to characteristic light emission at low pressure. However, the emitted light has a very complex relationship to the initially excited states at higher pressures since various collisions can alter the distribution of excited species. Also, there are difficulties connected with the detection of light, i.e., the efficiency is relatively low and usually not quantitative.

Thus, there exists a need for an improved method and means for generating selected excited states of a gas to be analyzed and for accomplishing a sensitive and absolute measurement of one or all of the excited states. This need has been accomplished in the present invention in a manner to be described below.

SUMMARY OF THE INVENTION

It is the principal object of the present invention to utilize the concept of generating ion pairs by a process which involves one or more excited states of a selected atom and to accomplish a sensitive and absolute means for the detection, or measurement, of the ion pairs.

It is also an object of the present invention to utilize resonance ionization for analytical spectroscopy and related applications.

The present invention is a method for the sensitive and selective analysis of an atomic or molecular component of a gas which comprises creating an excited energy state of the component, totally ionizing the excited state by at least one resonance photon absorption, and accurately measuring a charge produced by the ionization.

The above objects may be accomplished in a number of manners, starting at the ground state of the atom, using two to three photons for accomplishing ionization, or one to three photons together with some additional process of ionizing a highly excited state. In each case, at least one step is resonance photon absorption and, under saturation conditions, the amount of ionization charge is an accurate measure of the quantity of the selected atom. Measurement of as little as a single atom is possible using this method.

DESCRIPTION OF THE PREFERRED EMBODIMENTS

Figure 1:
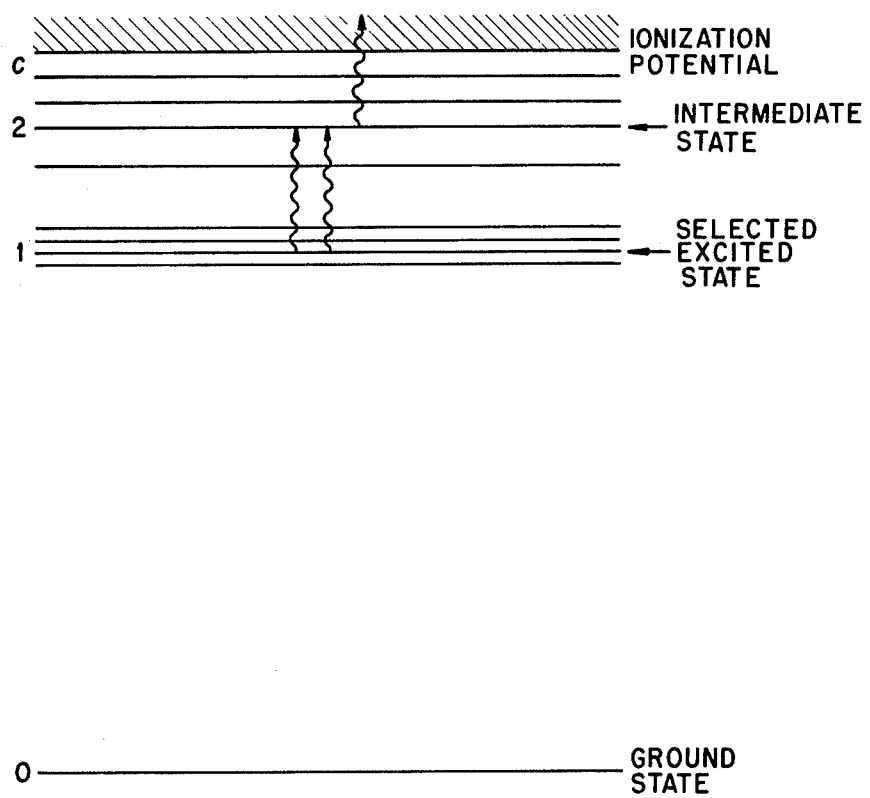
FIG. 1 is a drawing showing energy levels of excited states typical of noble gases as well as the ionization level of the atom.
Figure 4:
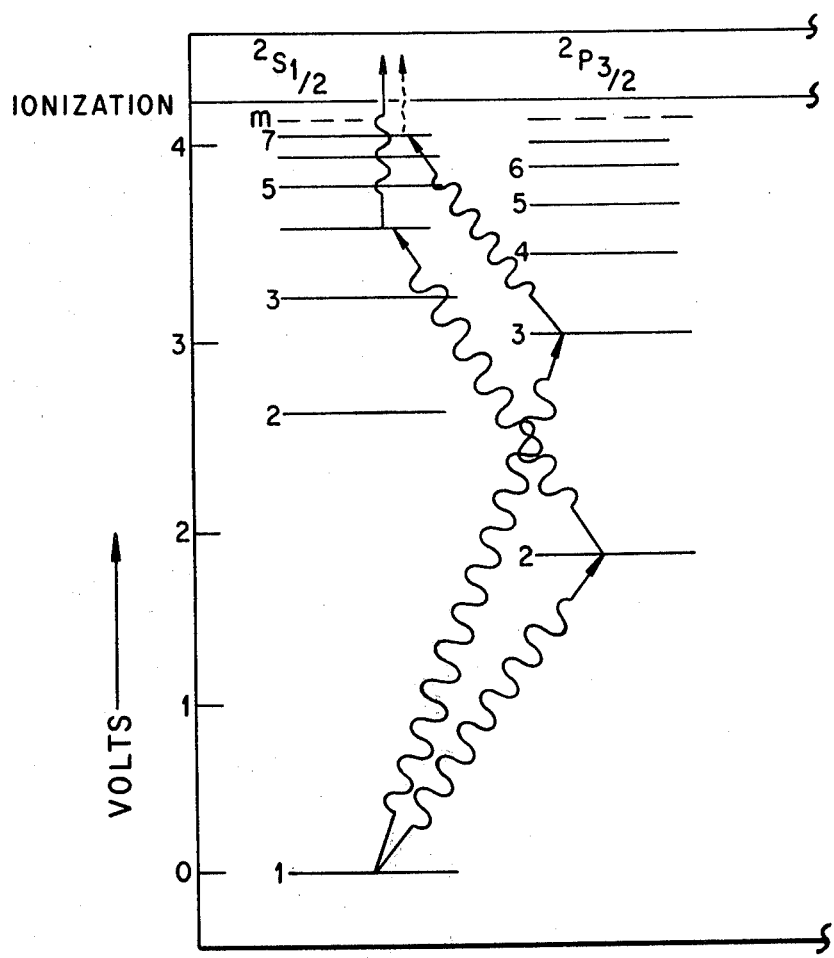
FIG. 4 is a drawing showing typical excited states of a metal atom together with the ionization level.

When a gaseous atom is subjected to an energy pulse from any suitable source, a number of excited states of the atom will be produced. Some of the longer-lived (metastable or resonance-trapped) states, situated at energy levels between the ground state and the ionization potential, are illustrated in FIGS. 1 and 4. These states and their location depend upon the particular atom. If the system is permitted to "relax," the excited states will decay to the ground state by light emission, or in more complex ways if atomic collisions occur. If, however, additional energy is put into the excited species by photon absorption before they decay, some or all may be ionized depending upon the photon energy. If only the highest excited state is ionized, the ionization charge would be relatively small, while if a sufficient number of high energy photons are introduced to ionize all states, the charge would be relatively large. Measurements via direct photon ionization of an excited state are obviously of little selectivity.

Figure 2:
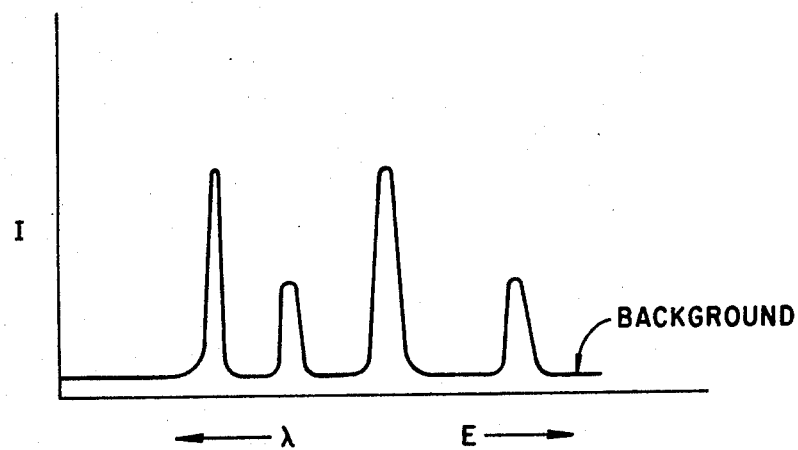
FIG. 2 is a graph illustrating the ionization current as a function of energy if the individual excited states of FIG. 1 are first excited to an intermediate state and then ionized according to the present invention.

In contrast, the resonance photoionization of the present invention can be used to identify and measure each excited state, i.e., energy resolution of each state is possible. According to the present invention, a multi-step photoionization is utilized. A laser beam directed at a gaseous target consisting of the excited species is tuned to resonate with the desired excited state and a state which is intermediate between the desired excited state and the ionization potential of the atom (see FIG. 1). If the intermediate level is chosen to lie above the excited state by more than half the distance between the excited state and the ionization limit, then a second photon from the laser beam (or a photon of sufficient energy from a second laser) will photoionize the intermediate excited level. Through the proper choice of photon energies, each excited state can be identified in the ionization charge as illustrated in FIG. 2. Furthermore, if the photon fluence per laser pulse is large enough to ionize all the excited species, the area under any peak is proportional to the absolute number of the respective excited states.

The initial creation of the excited states may be accomplished in several ways. Typical methods known in the art include the use of pulsed energetic protons (e.g., 2 MeV), electron guns, x-rays, radioactive particles, gas discharges, shock tubes, microwave sources and lasers. The choice depends, in part, on the availability, convenience and particular application. All of the named methods, except the electron gun and laser produce "background" in the measured ionization. That is, there is some direct ionization that must be taken into account in analyses.

Figure 3:
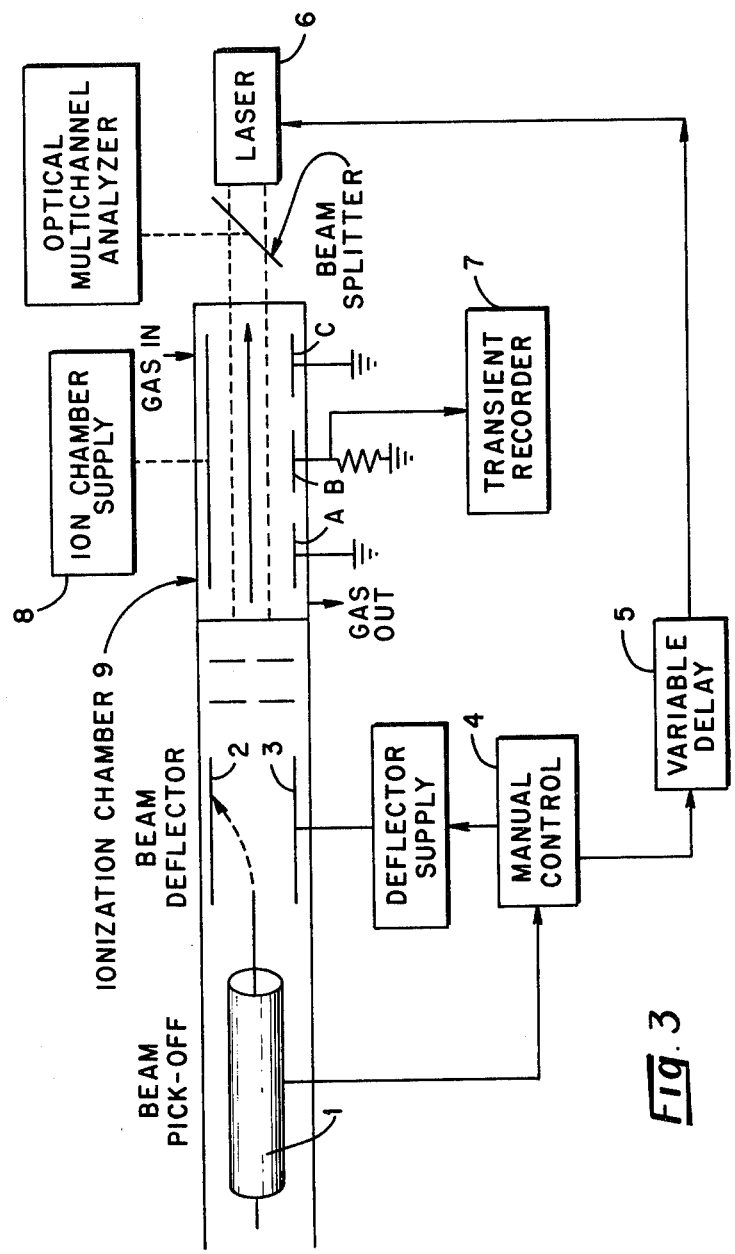
FIG. 3 is a drawing illustrating apparatus for obtaining the information such as shown in FIG. 2.

Studies were initiated of resonance ionization spectroscopy using helium as a target gas and 2 MeV protons from a Van de Graaff accelerator as the means for producing the metastable (excited) states. The drawing of FIG. 3 illustrates the apparatus for these studies. A stream of proton bursts from an accelerator 1 entered a set of deflector plates 2, 3 which normally deflected all the bursts from the reaction cell 9 (ionization chamber) connected to an ion chamber supply 8. On manual command from a control 4, one pulse of protons was allowed to enter the cell 9. An adjustable delay generator 5 was used so that a photon pulse from a tunable dye laser 6 was caused to enter the reaction cell 9 at any selected time with respect to the arrival of the proton burst. The pulse from the delay generator also triggered the sweep of a transient recorder 7 which recorded the amplified electrical signals from the reaction cell.

In operation, the proton beam burst produced charged particles and excited states in the gas. The charged particles alone produced an electrical signal at plates A, B, and C proportional to the number of ion pairs created. At a pre-selected time later, a photon burst, with the photons tuned to the correct wavelength, ionized the atoms in the excited state being studied. A second signal was produced at plates A, B, and C by these charged particles which was separated in time from the proton produced signal.

The laser was used to generate 0.69 Joule pulses lasting 0.3 $\mu$ sec. and having a wavelength centered at 5015 A; the line width was $\sim$ 30 A. This wavelength was chosen to create He($3'P$) as the intermediate state. The laser pulses were fired into a gas cell filled with He (99.9995% pure) at various times following excitation by pulses of $10^3 - 10^4$ protons. Signals generated by the direct ionization of the protons and by the resonant ionization of He($2^1S$) by the laser pulse were recorded by the transient recorder. From the ratio of pulse heights, the number of ion pairs due to the laser pulse divided by the number of ion pairs produced by the protons was determined. It was demonstrated that: (1) the laser pulse could be attenuated by a factor of $\sqrt{10}$ without appreciably reducing the ratio, and (2) the laser beam could be spread by a lens (so that its radius in the interaction region was increased by a factor of $\sim$2) without appreciably changing the ratio. Thus, as suggested by theory, it appeared that the ionization was saturated and the spatial overlap was complete so that the measured ratio represented the ratio of the He($2^1S$) population to the number of ion pairs produced during and just after the passage of the protons.

Although the use of a Van de Graaff accelerator is satisfactory for fundamental studies, it would be inconvenient for any routine resonance ionization spectroscopy. Much more desirable would be a laser to create the excited states. However, in some applications like the noble gases, an energetic laser of the proper wavelength is not presently available. Although frequency doubling is possible, a significant energy loss is encountered. It is expected, however, that future lasers will cover the range from about 2400 A. to 7200 A.

As an illustration of the absolute features of the method, whenever a dye laser at 1 Joule per pulse is tuned to approximately 5000 A. the number of photons per pulse is approximately $2.5 \times 10^{18}$, and if the beam area is 1 cm$^2$, a photon fluence of $2.5 \times 10^{18}$/cm is produced. If an atom in its ground state can be promoted to an excited level by a 5000 A. photon, its excitation cross section is so large that the excited level immediately comes into equilibrium with the ground state. Photoionization of the excited state, however, is more typically $4 \times 10^{-18}$/cm. Even with this small cross section, the product of fluence times cross section is about 10. Whenever this product is greater than 1, an appreciable fraction of the ground state atoms are converted to ions; for example, when the product is 3, about 95% of the atoms are ionized and more than 99% are ionized when the product is 10.

There are many elements, such as a number of metal vapors, for which the present lasers (3900 A. - 7400 A.) have application. A portion of a typical energy level diagram of such an element (potassium) is illustrated in FIG. 4. Here it may be seen that the photons of one laser may excite the atom from the ground state to a relatively nearby excited state ($^2P_{3/2}$, $m = 2$), another photon (from a second laser) in resonance then exciting the atom to a level such as $m = 4$ of $^2S_{1/2}$, and then a laser pulse from either laser would bring about ionization of the atom. This is an example of three photon ionization in contrast to the previously described two photon ionization. Alternatively, one photon could raise the atom to $m = 3$ of $^2P_{3/2}$ prior to excitation to the intermediate state at, for example, $m = 5$ or higher (the intermediate level must be more than one-half the distance between the first excited state and the ionization potential).

Still other resonance ionization methods are possible using lasers. For example, one or two photons can be used to raise the energy to a point near ionization, e.g. $m = 7$ (FIG. 4). Then in the presence of a ground-state atom at moderate pressures, associative ionization takes place according to the equation:

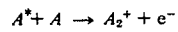

It is also known that certain compounds promote ionization through a process called chemi-ionization. One such compound is SF$_6$. Accordingly, this process may be coupled with the use of one or more photons (at least one in resonance with an elevated energy state) according to the equation:

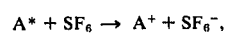

where A* has an energy very near the ionization potential.

Still another form of ionization that may be applied to very highly excited atoms is Penning ionization when the ionization potential of A is sufficiently high. Two photons from one or more lasers (one photon in resonance with the desired highly excited state) would create the desired excited state, and ionization would occur according to the equation:

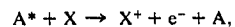

where X is any substance whose ionization potential is less than the energy of A*.

Still another excitation process for accomplishing final ionization is that of using an electric field. This may be used when the excited state is at an energy very close to the ionization potential (a high Rydberg state).

Whenever one or more of the various excitation processes illustrated above are utilized, the laser energy per pulse can be greatly reduced because the resonance cross sections are very large as described above.

A typical laser useful for obtaining the desired resonance for any of the above-described embodiments of resonance ionization spectroscopy is a tunable pulsed dye laser such as that manufactured by Phase-R Corporation, New Durham, New Hampshire. In the range of 4250 – 7400 A. each pulse contains in excess of one Joule of energy, i.e., in excess of $10^{18}$ photons. Furthermore, the beam diameter is of the order of 1 cm². This provides the advantage that a relatively large volume of a sample is intercepted by the laser beam.

Figure 5:
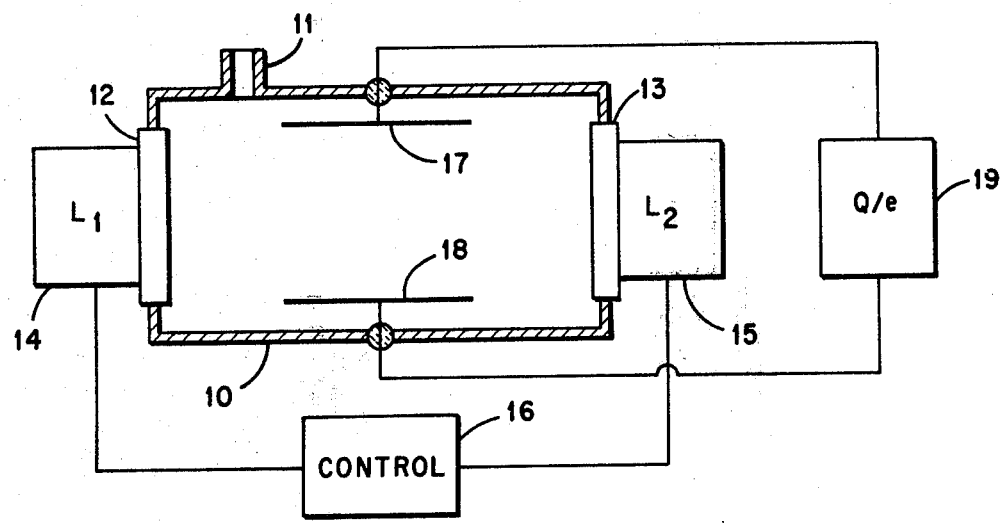
FIG. 5 is a schematic block diagram of one form of apparatus for accomplishing analytical spectrometry using two lasers and the method described herein.

One apparatus for accomplishing such analyses is shown in FIG. 5. A container 10 communicating with a tube 11 for the admittance of gas to be analyzed is provided with a pair of windows 12, 13 for admitting light from a pair of laser units 14, 15. Laser 14, which is tuned for bringing about excitation of the desired states of an atom to be measured, may be, for example, the same laser described above but equipped with a frequency doubling crystal (if necessary) thus extending the photon energy of about 6 ev. The second laser 15 is a tunable pulsed laser such as the aforementioned laser manufactured by Phase-R Corporation. Proper initiation of pulses by lasers 14, 15, in the necessary time sequence is achieved through a control unit 16. Inserting a pair of parallel plates 17, 18 within the container provides an ionization chamber suitable for collecting the ionized species. A charge-measuring unit 19 is connected across plates 17, 18 whereby the total charge, Q, divided by the charge on the electron, e, is the total number of atoms of a substance. By proper tuning of each laser, high selectivity of the desired atom and discrimination against background ionization is achieved. Since the energy of excited states of most substances is known, the necessary energy and wavelengths for the lasers may be set to provide a highly useful analytical spectrometer.

As little as one atom may, in principle, be measured using the present invention. For this extreme measurement, the container 10 may be operated as a Geiger counter with a central wire (not shown) in place of plates 17, 18. Since a Geiger counter is capable of detecting one free electron, the Q/e can be equal to unity. This demonstrates the ultimate sensitivity of the method.

Figure 6:
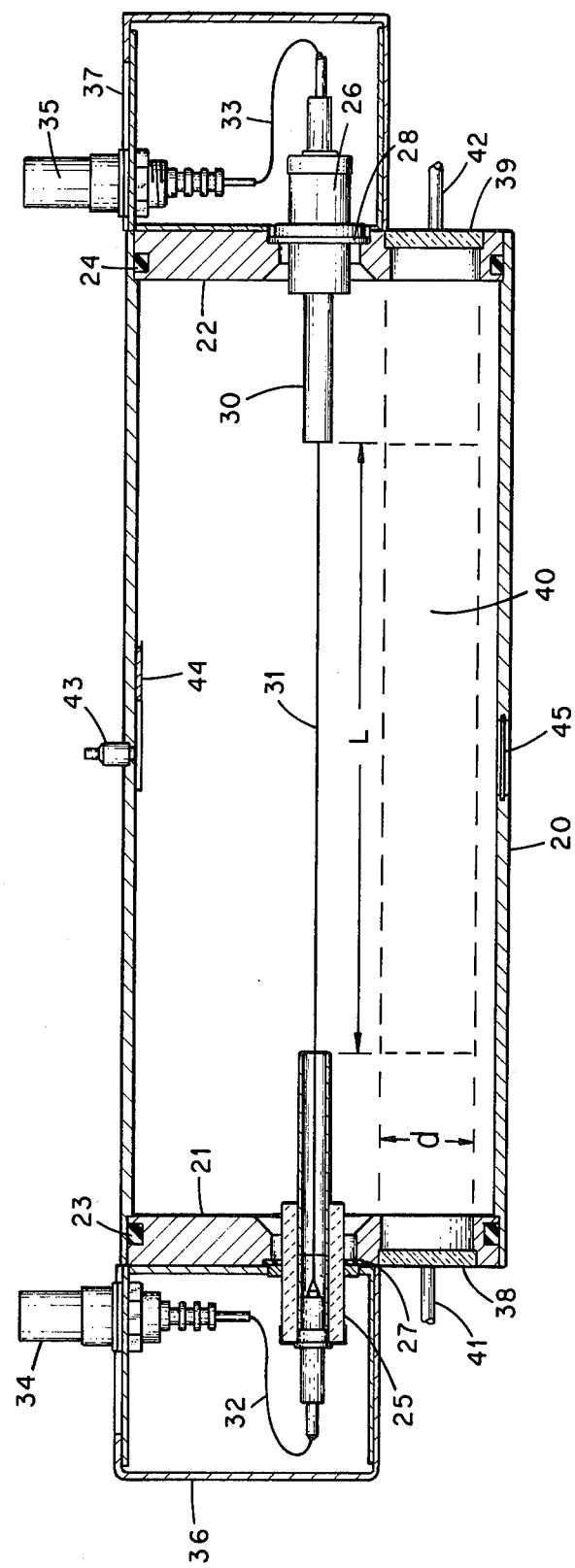
FIG. 6 is a cross sectional drawing of a second form of apparatus for accomplishing analytical spectroscopy using the method disclosed herein.

More generally, for measurements in the range of one to $10^5$ atoms, a proportional counter type chamber may be preferred such as illustrated in FIG. 6. A body shell 20 is provided with a pair of removable end walls 21, 22, and the junctions therebetween are provided with seals 23, 24. Centrally located in the end walls 21, 22 are insulators 25, 26 enclosed by seals 27, 28. Passing through these insulators 25, 26 are tubes 29, 30 which are field tubes to define the active length, L, of a collector wire 31 passing along the length of the counter and being centrally located within the tubes 29, 30. The collector wire 31 is connected by leads 32, 33 to connectors 34, 35 mounted in respective end chambers 36, 37. The connectors 34, 35 are coupled to an external counter, not shown.

The end walls are also provided with a pair of opposed photon transparent windows 38, 39. The effective diameter, d, of these windows 38, 39 produces an effective interaction volume 40 within the chamber. Further, the end walls 21, 22 are provided with gas tubes 41, 42 (in a different plane than the windows 38, 39) to permit flow-through operation of the gas under analysis. Depending upon the type of final ionization step, as discussed above, other gases (e.g., $SF_6$) may be introduced with the sample gas or through other ports (not shown).

As is customary practice, to assist in calibration of the proportional counter, an alpha source 43 and shutter 44 are provided in the side wall of shell 20. Furthermore, a thin window 45 is provided in the wall of shell 20 opposite the source 43 which allows for the introduction of soft x-rays as an alternative method of calibration.

Not shown in this figure are the two tunable dye pulsed lasers that would be positioned adjacent respective windows 38, 39. Also, the voltage supply for the chamber, the switching circuits and the charge measuring elements are not shown. These would be similar to those shown in FIG. 3 or FIG. 5.

Ions produced according to the above-described methods may also be counted in an evacuated electron multiplier counter, if such is desired.

A closely related application of the above-described devices and method is in leak detection. For such use the lasers would be set at values for helium or whatever other gas is used for leak searching. Since most systems to be leak checked are under high vacuum, an electron gun (not shown) may be used for initial excitation. In this application, the means of charge measurement need not be absolute because normally only qualitative indication of the presence of helium is desired.

There are other applications of the present invention that do not require the measurement of charge, at least in any accurate manner. This further relaxes the specification on the excitation means since background ionization is not detrimental and rather may be beneficial. One such application is the removal of one gas from a system in the presence of another. For example, amounts of metal vapor present in otherwise pure gas could be removed. The laser for photoionization would be set for ionizing all of the excited species of the metal vapor and the ions would be collected to bring about purification of the gas. The required number of pulses of the laser would depend upon the concentration of the impurity. Application of such a technique may be important in purification of materials for semi-conductor crystal growing, for example.

This invention has been described by way of illustration rather than by limitation and it should be apparent that it is equally applicable in fields other than those described.

What is claimed is:

1. A method for the sensitive and selective analysis of an atomic or molecular component of a gas in an ion measuring chamber, comprising the steps of exciting said component to a first excited state, further exciting said component to a second and higher energy excited state from said first state through resonance photon absorption, said second excited state being at an energy level greater than one-half the energy between said first excited state and the ionization potential of said component, ionizing said component from said second excited state, and measuring the ions produced by the ionization within said chamber.

2. The method set forth in claim 1, wherein said resonance photon absorption is effected by a first tuned pulsed dye laser.

3. The method set forth in claim 1 wherein said first excited state is produced by resonance photon absorption effected by a second tuned pulsed dye laser.

4. The method set forth in claim 1 wherein said first excited state is produced by energetic electrons.

5. The method set forth in claim 1 wherein said ionization of said second excited state is effected by photo absorption.

6. The method set forth in claim 1 wherein said ionization of said second excited state is effected by chemi-ionization.

7. The method set forth in claim 1 wherein said ionization of said second excited state is effected by associative ionization.

8. The method set forth in claim 1 wherein said second excited state is at an energy very near the ionization potential, and said ionization of said second excited state is effected by the application of an electric field within said chamber.

9. The method set forth in claim 1 wherein said ionization of said second excited state is effected by Penning ionization.

10. The method set forth in claim 1 wherein all of said second excited state is ionized whereby the measured ionization is an accurate measure of the concentration of said component in said gas.

* * * * *